United States Patent
DeCandia et al.

(10) Patent No.: US 6,174,399 B1
(45) Date of Patent: Jan. 16, 2001

(54) METHOD OF MAKING AN ELASTIC ADHESIVE BANDAGE

(75) Inventors: Len C. DeCandia, Springfield; Philip DeSalvo, Cranbury, both of NJ (US)

(73) Assignee: Johnson & Johnson Consumer Companies, Inc., Skillman, NJ (US)

( * ) Notice: Under 35 U.S.C. 154(b), the term of this patent shall be extended for 0 days.

(21) Appl. No.: 09/177,478

(22) Filed: Oct. 22, 1998

Related U.S. Application Data

(63) Continuation of application No. 08/876,553, filed on Jun. 16, 1997, now abandoned, which is a continuation of application No. 08/537,022, filed on Oct. 2, 1995, now abandoned, which is a continuation of application No. 08/224,922, filed on Apr. 8, 1994, now abandoned.

(51) Int. Cl.⁷ .............. B32B 31/18; B26D 3/00; B65H 23/182; A61F 13/00
(52) U.S. Cl. .......... 156/229; 156/250; 156/270; 156/271; 156/289; 83/343; 226/4; 226/112; 602/42; 602/52; 602/54; 602/57; 602/58
(58) Field of Search .................. 156/227, 197, 156/196, 250, 251, 287, 290, 324, 270, 271; 602/42, 45, 46, 52, 54, 57, 58; 83/343; 226/4, 112

(56) References Cited

U.S. PATENT DOCUMENTS

| | | | |
|---|---|---|---|
| 4,622,089 | * 11/1986 | Lauritzen | 156/250 |
| 4,969,970 | * 11/1990 | Suzuki et al. | 156/495 |
| 5,024,128 | * 6/1991 | Campbell, Jr. | 83/26 |
| 5,190,233 | * 3/1993 | Nelson et al. | 242/56 R |

\* cited by examiner

Primary Examiner—James Sells
Assistant Examiner—J. A. Lorengo

(57) ABSTRACT

Adhesive bandages are prepared from an elastic backing material by decreasing the tension in the backing material just prior to attachment of the adhesive pad.

5 Claims, 3 Drawing Sheets

METHOD OF MAKING AN ELASTIC ADHESIVE BANDAGE

This application is a continuation of Ser. No. 08/876,553, filed Jan. 16, 1997, now abandoned, which is a continuation of Ser. No. 08/537,022 filed Oct. 2, 1995, now abandoned, which is a continuation of Ser. No. 08/224,922, filed Apr. 8, 1994, now abandoned.

FIELD OF INVENTION

The present invention relates a method of manufacturing a multi-layered adhesive bandage wherein one of the layers is an elastic, preferably foam material. More particularly, this invention relates to a method of manufacturing adhesive bandages comprising an elastic, foam backing sheet and an absorbent, central pad adhesively attached to the backing sheet.

BACKGROUND OF THE INVENTION

Adhesive bandages comprising a central pad area and adjacent adhesive areas are well-known in the art and popular as first aid wound dressings. Current bandages generally comprise an elongated strip of cloth or plastic backing material coated on one surface with a pressure sensitive adhesive. A gauze or sponge pad is secured to the adhesive surface in a central location to serve as the wound cover. The wound facing surface of the pad may be plastic-coated or otherwise treated to prevent the pad from adhering to the wound. Plastic-coated release strips are placed over the adhesive areas and the entire assembly is placed in a sealed package and sterilized to be ready for use.

The adhesive bandages of the prior art are characterized by their construction of two basic components: (1) the adhesive coated backing material and (2) the wound covering pad material. The pad material may be dry or impregnated with various bactericides or other wound treatment medicaments. The capacity of the pad to absorb and hold such compositions is a limiting factor on the amount of such material which may be incorporated into the bandage.

Such prior art bandages, while serving well their purpose in an earlier day, tend to be stiff and non-pliable. Consequently, when they are used to cover a wound on, for instance, a joint such as an elbow, depending on the orientation of the elbow, the bandages will not stretch sufficiently to allow full range of motion. Or, if the bandages are applied while the elbow is bent, the bandages will tend to disengage from the wound when the arm is fully extended, exposing the wound to the elements from which it should be protected. Further, bandages in the prior art tend to be thin, a consequence of traditional manufacturing processes where, in order to achieve high production rates, much tension is placed on the various layers. This tension tends to draw down the layer thickness.

In today's active world, people desire a bandage which will conform to their bodies, no matter where the wound is, and protect and cushion the wound from further injury until it is healed. The necessary characteristics of such a bandage include a certain degree of elasticity which will allow full range of movement while still keeping the wound covered. Further, such a bandage will also have a certain amount of cushioning thickness to protect the wound until it is fully healed.

It is an object of the present invention to provide an improved adhesive bandage meeting the characteristics discussed above. This and other objects of the present invention will be apparent from the ensuing description and claims of the invention.

SUMMARY OF THE INVENTION

A method for manufacturing an elastic adhesive strip bandage is provided, which method comprises the steps of:
 (a) stretching an elastic backing layer;
 (b) relaxing the elastic backing layer;
 (c) placing an absorbent layer on the elastic backing layer forming a laminate; and
 (d) cutting the laminate into strips.

Adhesive bandages comprising an elongated strip of material having a centrally-located blister pad and adjacent adhesive portions extending from each side of the pad area are prepared from an elastic backing material. The blister pad is applied to the center of the bandage strip and secured by, for example, adhesives. A medicated gel or other material may be deposited on the bandage strip and covered with the blister pad to provide a medicated bandage. The bandage strip is preferably left uncompacted to retain soft and absorbency, but the pad may be heat glazed to provide a nonadhering wound release surface.

Strip bandages are conveniently prepared according to the present invention from a first, continuous base material having a width equal to the overall length of the desired bandage, and a second, continuous pad material having a width at least equal to the desired pad area. The base material is fed by a vacuum drum where the moving velocity of the base material is increased slightly. Downstream of the vacuum drum, the velocity of the base material is then slowed so that the elastic nature of the material is allowed to relax. It can next passed through a station (not shown) where a medicated gel or other material can be deposited onto the center of the moving strip if desired. The pad material is then applied to the relaxed base material.

Adhesive release liners are applied and the composite structure fed to a cutting station where strips are cut or stamped transversely to machine direction of the base and pad materials to obtain individual adhesive bandages. The resulting bandages are ready to be packaged and sterilized.

The material used in the fabrication of the base or backing layer of the bandages according to the present invention is preferably an elastic film or foam material that can be elastically stretched in any direction.

DETAILED DESCRIPTION OF THE INVENTION

The strip adhesive bandages of the present invention are fabricated from continuous lengths of bandage material which are preferably elastic foams or films. The bandage is fabricated by positioning the pad material over the center area of the backing material, securing the pad by, preferably adhesives, and applying release strips. The laminate is then cut transversely to its machine direction in strips to the width of the desired bandage. A useful process which generally describes the manufacture of bandages is found in U.S. Pat. No. 4,622,089 (Lauritzen), which is hereby incorporated in its entirety by reference.

A backing material meeting the desirable characteristics of bulk for cushioning and elasticity for secure placement and conformability to the body is a plasticized PVC foam material. Such a material is described in co-pending U.S. patent application Ser. No. 08/225,171, filed Apr. 8, 1994, now abandoned which is assigned to the same assignee as this invention and is also hereby incorporated in its entirety by reference. Many different types of backing materials are usable in this process, but most preferable is a PVC elast foam product with a bulk density of about 30 pounds per cubic foot and preferably about 20 mils thick sold by Gaska Tape, Inc. of Elkart, Indiana. For the sake of simplicity, the remainder of this description will refer to this specific elastic material. However, all materials refered to in the co-pending application noted above are suitable as well.

Figure 1:
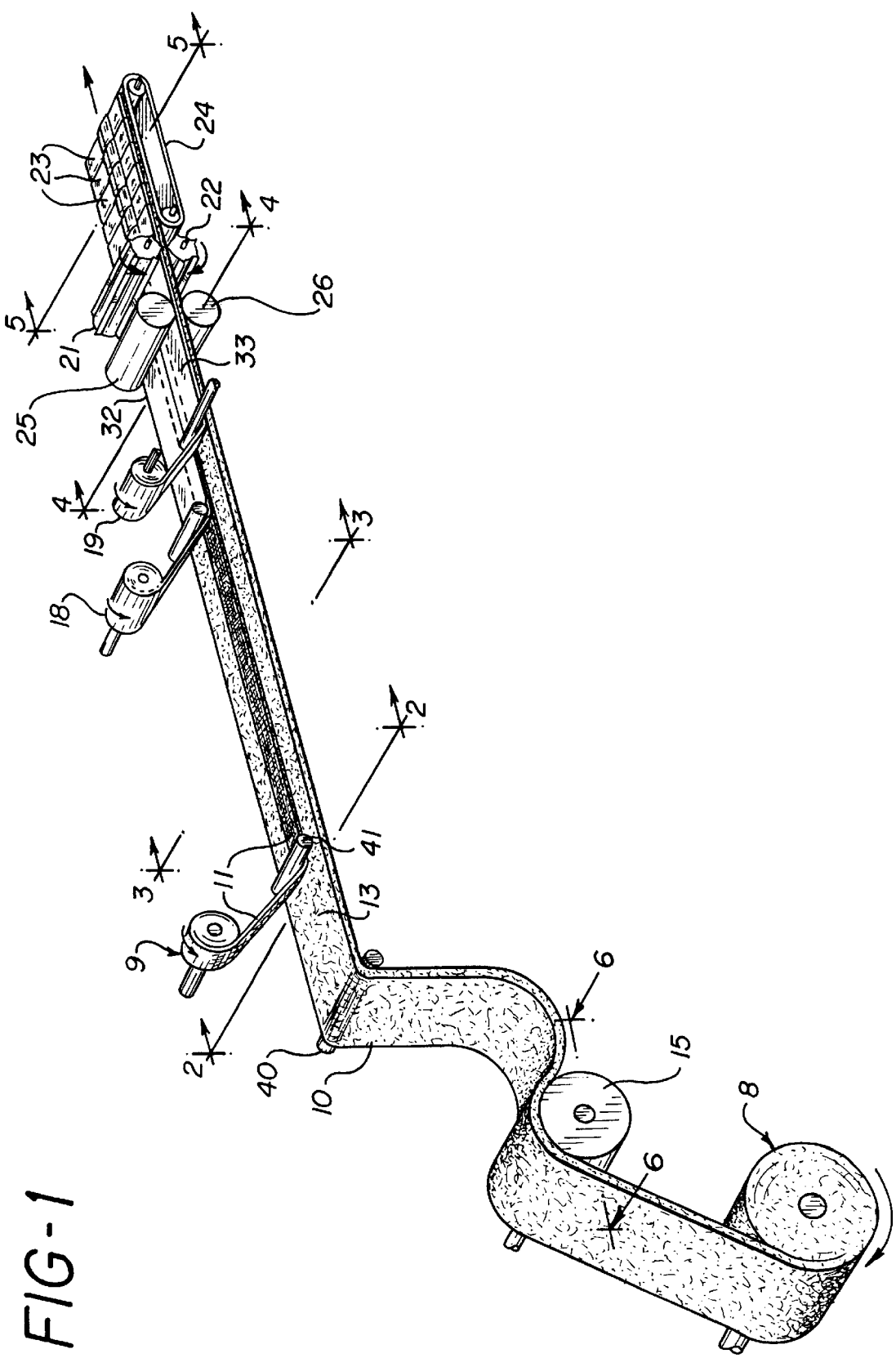
FIG. 1 is schematic representation in perspective of a process used to produce strip adhesive bandages of the present invention.
Figure 2:
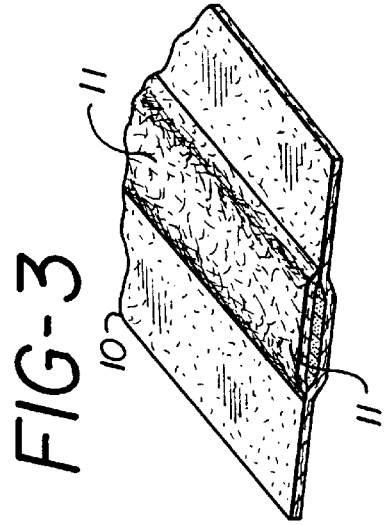
FIG. 2 is a cross-sectional view in perspective of the backing material of FIG. 1 through line 2—2.
Figure 3:
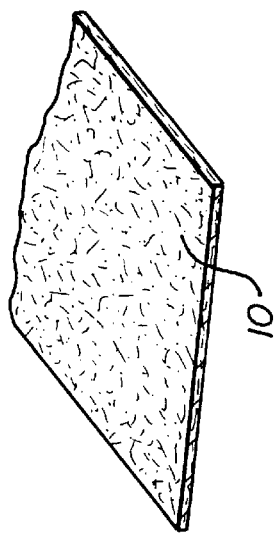
FIG. 3 is a cross-sectional view in perspective of the backing material after application of the pad, through line 3—3 of FIG. 1.
Figure 4:
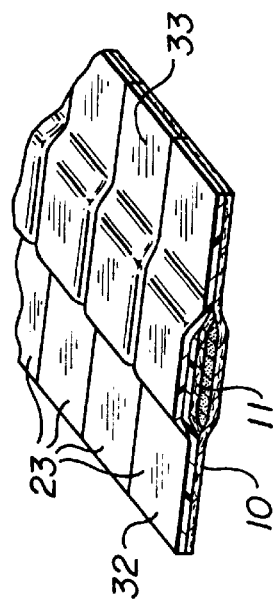
FIG. 4 is a cross-sectional view in perspective of the backing material and pad after application of release strips, through line 4—4 of FIG. 1.
Figure 5:
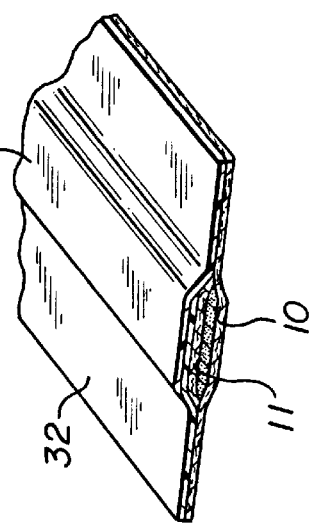
FIG. 5 is a cross-sectional view in perspective of the backing material and pad after cutting into strips, through line 5—5 of FIG. 1.

The process of preparing adhesive strip bandages from continuous rolls of elastic PVC foam material will be better understood by reference to FIGS. 1 through 6. In FIG. 1, the elastic base material 10, which comprises pre-made elastic PVC foam, fed from roll 8 passes over vacuum drum 15, where, as it will be described more fully below, the tension in the elastic base material 10 allowed to relax. The elastic base material 10 then passes over idler roll 40. At this point, and although it is not shown, medicated gel or other material may be deposited onto the center line of the backing material fabric. Nonwoven pad fabric 11 feeding from roll 9 passes under idler roll 41 which is adjusted to provide clearance for any gel between the pad fabric 11 and elastic base material 10. To the laminate comprising the elastic base material 10 and the pad fabric 11 are applied release papers 32 and 33 fed from rolls 18 and 19 respectively. The release papers preferably overlap along the center of the web over the pad area. FIG. 4 is a view in cross section of the composite material after application of the release papers.

The composite material next passes through a cutting station where cutters 21 and 22 cut the material into transverse strips 23. The cut strips are carried on conveyor belt 24 to a packaging station (not shown) where individual strips are packaged in sealed envelopes prior to sterilization. The cut strips 23 are further illustrated in cross section in FIG. 5.

In order to assure that the various layers of the bandage remain together it is preferable that they be adhered by the use of adhesives. The adhesive is preferably applied by transfer coating or other convenient method to provide a continuous coating of adhesive over the surface of the elastic base material 10 to which the pad fabric 11 and the release strips 32 and 33 are attached. Transfer coating is well known in the art as is direct application adhesive materials as taught, for example, in U.S. Pat. No. 4,622,089.

In a typical manufacturing operation, in order to achieve maximum throughput, the composite materials are fed continuous at a set speed into the cutters 21 and 22. In FIG. 1, feed rolls 25 and 26 supply the necessary velocity and control to the composite material making up the bandage. As such, feed rolls 25 and 26 pull the bandage material from rolls 8, 9, 18, and 19. Preferably the speed of rolls 25 and 26 are computer controlled. Since the base material 10 is elastic, if the feed rolls 25 and 26 were simply allowed to pull this material from roll 8, the material would simply draw down due to the tension and this tension would not be released prior to the cutting step. Thus, without the vacuum drum 15, the resultant bandages would either not be cut to the proper size or would not have sufficient elasticity to conform to the wound area.

The vacuum drum serves to pull the elastic base material from roll 8. It "grips" the material by application of a vacuum (not shown) on the base material. This allows the elastic base material to be withdrawn from roll 8 independent of the rate at which the pad fabric 11 and the release strips 32 and 33 are withdrawn from rolls 9, 18 and 19. By controlling the speed of the motor on the vacuum drum 15 (not shown) it is possible to release the tension on the elastic base material 10 prior to application of the pad fabric 11. Preferably, the vacuum drum is run so that the velocity of the elastic base material 10 as it is unwound from roll 8 is slightly faster than the velocity of the pad fabric 11 as it is unwound from roll 9. This causes some slack in the strip of the elastic base material 10. This slack allows the elastic nature of the material to relax from the tension caused from the unwinding and isolates the roll 8 from the feed rolls 25 and 26.

Preferably the speed of the vacuum drum 15 is computer controlled and the velocity of the elastic base material is from 5% to 25% faster than the velocity of the other materials going into the bandage make-up. More preferably, the speed of the elastic base material is from 10% to 15% faster.

Figure 6:
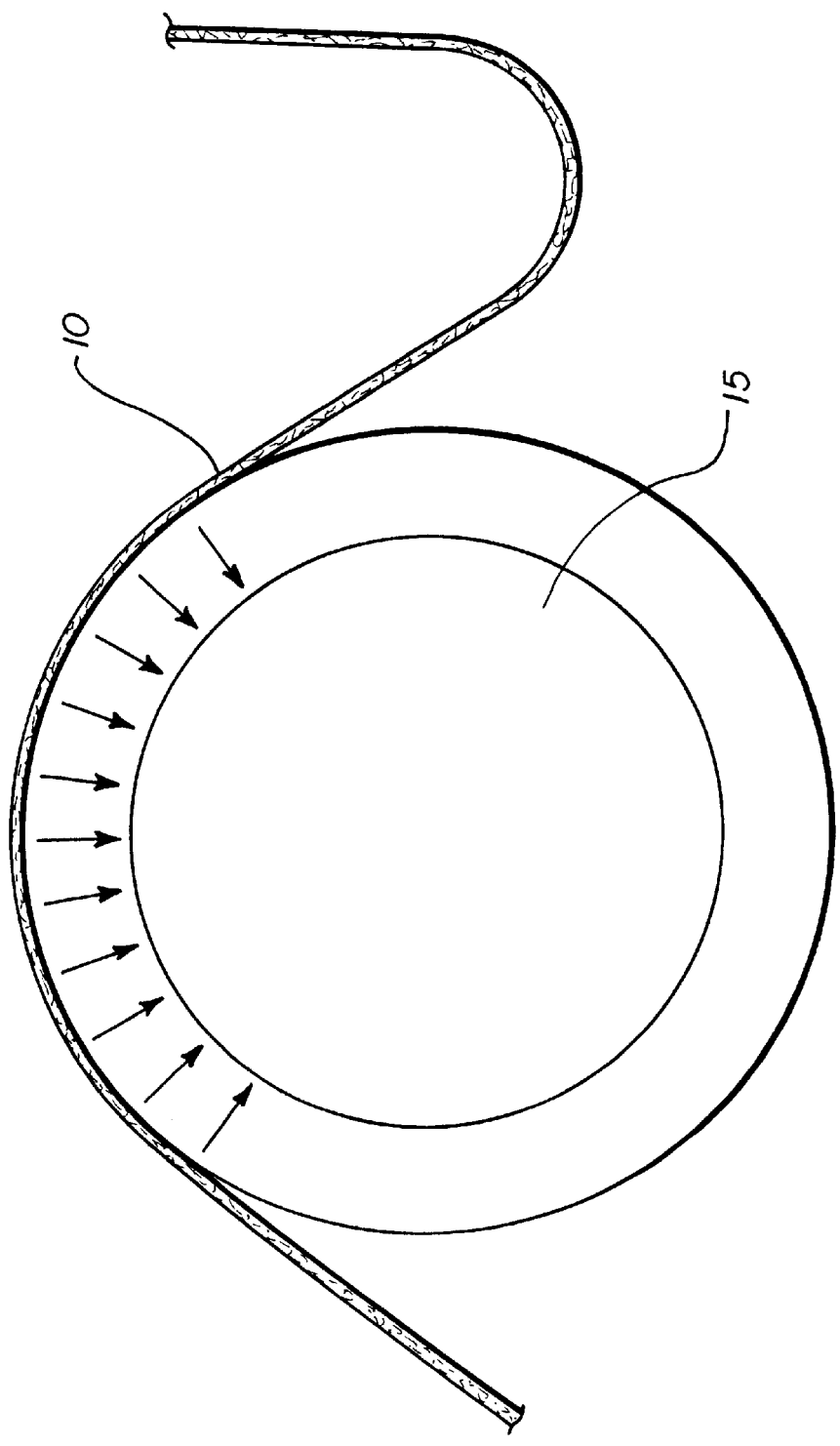
FIG. 6 is a cross-sectional view of the vacuum drum after the elastic base material is unwound, through line 6—6 of FIG. 1.

Looking at FIG. 6, the elastic base material 10 is engaged with vacuum drum over a 0 to 180 arc. The amount of contact, though, is not critical to the operation of this process. What is necessary is that the vacuum drum isolate the roll 8 from the tension caused by the feed rolls 25 and 26. The vacuum drum consists of an inner plenum surrounded by an outer perforated plate. The plenum is constructed so that air can be drawn through the perforated plate and into the plenum over the necessary arc length to grip the elastic base material 10. A vacuum is drawn with air flow indicated by the arrows. Again, the amount of vacuum is not critical and should be easily ascertained with minimal experimentation.

As stated above, the speed of the vacuum drum 15 is controlled so that, by its rotational speed, it causes the elastic base material 10 to be drawn from roll 8 faster than the other materials going into the bandage are being fed into the process. This allows the elastic base material 10 to slacken after the vacuum drum. This slack then allows the elastic base material 10 to be drawn into the remainder of the process with minimal tension.

Other means may be available to isolate the tension caused by the feed rolls 25 and 26. For instance, instead of a vacuum drum 15, additional feed rolls may be used. However, additional feed rolls may tend to compress the elastic material leaving it less bulky and, hence, with less of a cushioning effect.

What is claimed is:

1. A method for manufacturing elastic bandages, comprising the steps of:
   (a) tensioning an elastic backing layer between a first supply roll and a vacuum drum by pulling the elastic backing layer from the first supply roll with the vacuum drum;
   (b) relaxing the elastic backing layer after the tensioning step, thereby forming a relaxed elastic backing layer;

(c) providing a second supply roll that contains a pad fabric and a third supply roll that contains a release material;

(d) using a pair of feed rolls to simultaneously (i) pull the relaxed elastic backing layer toward the pair of feed rolls, (ii) pull the pad fabric from the second supply roll toward the pair of feed rolls, and (iii) pull the release material from the third supply roll toward the pair of feed rolls;

(e) forming a composite material by applying the pad fabric and the release material to the relaxed elastic backing layer as the relaxed elastic backing layer, the pad fabric and the release material are being pulled by the pair of feed rolls; and (f) cutting the composite material into strips in order to form the elastic bandages;

said elastic backing layer being pulled from the first supply roll by the vacuum drum at a first rate of speed, and the relaxed elastic backing layer, the pad fabric and the release material being pulled by the pair of feed rolls at a second rate of speed that is independent of the first rate of speed, thereby causing formation of a slack in the relaxed elastic backing layer between the vacuum drum and the pair of feed rolls.

2. The method of claim 1, wherein step (f) comprises:

(f) after step (e), cutting with a cutting assembly, the composite material into strips in order to form the elastic bandages; wherein the first, second and third supply rolls are positioned on one side of the feed rolls and the cutting assembly is positioned on an opposite side of the feed rolls.

3. The method of claim 2, wherein step (e) further comprises centering a width of the pad fabric on a width of the relaxed elastic backing layer as the relaxed elastic backing layer and the pad fabric are respectively pulled by the pair of feed rolls, and step (f) further comprises cutting the composite material into narrow strips across the width of the relaxed elastic backing layer.

4. The method of claim 3, wherein steps (a)–(f) are performed in a continuous process.

5. The method of claim 4, wherein the elastic backing layer, the pad fabric and the release material are each supplied from the first, second and third supply rolls, respectively, in the form of a continuous, unbroken strip.

* * * * *